United States Patent [19]

Hatayama et al.

[11] Patent Number: 4,472,411
[45] Date of Patent: Sep. 18, 1984

[54] 1,4-DIHYDROPYRIDINE DERIVATIVES AND USE AS VASODILATORS

[75] Inventors: Katsuo Hatayama, Omiya; Aturo Nakazato, Saitama; Toshihisa Ogawa, Ageo; Shoichi Ito; Jiro Sawada, both of Tokyo, all of Japan

[73] Assignee: Taisho Pharmaceutical Co., Ltd., Japan

[21] Appl. No.: 486,508

[22] Filed: Apr. 19, 1983

[30] Foreign Application Priority Data

Apr. 22, 1982 [JP] Japan .................................. 57-67759

[51] Int. Cl.³ .................... C07D 211/90; A61K 31/44
[52] U.S. Cl. ...................................... 424/266; 546/321
[58] Field of Search ........................ 546/321; 424/266

[56] References Cited

U.S. PATENT DOCUMENTS 3,485,847 12/1969 Bossert et al. ...................... 546/321

FOREIGN PATENT DOCUMENTS 2847236 5/1980 Fed. Rep. of Germany .

Primary Examiner—Henry R. Jiles
Assistant Examiner—Dale A. Bjorkman
Attorney, Agent, or Firm—Kenway & Jenney

[57] ABSTRACT

The compounds of the formula

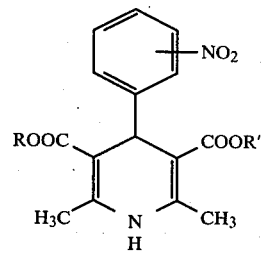

wherein R is alkyl having 1 to 4 carbon atoms or nitratoalkyl having 2 or 3 carbon atoms, and R' is nitratoalkyl having 2 or 3 carbon atoms, are disclosed. These compounds are useful as therapeutic agents for cardiovascular disorders such as coronary artery disease, cerebral artery disease, hypertension and the like.

5 Claims, No Drawings

1,4-DIHYDROPYRIDINE DERIVATIVES AND USE AS VASODILATORS

The present invention relates to novel 1,4-dihydropyridine dicarboxylic acid nitratoalkyl esters which have high and sustained vasodilatatory activity when administered orally, parenterally, rectally or topically. In particular, the structures of the vasodilatatory active compounds of the present invention are characterized by having one or two nitratoalkyl esters at the 3- and/or 5-positions of the 1,4-dihydropyridine.

The compounds of the present invention are represented by the formula

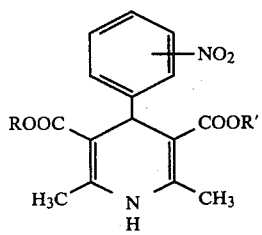
I wherein R is alkyl having 1 to 4 carbon atoms or nitratoalkyl having 2 or 3 carbon atoms, and R' is nitratoalkyl having 2 or 3 carbon atoms.

The present invention also relates to a method for treating cardiovascular disorders in a mammal comprising administering to said mammal a pharmaceutically effective amount of a compound of formula I.

The term "alkyl having 1 to 4 carbon atoms" refers to straight or branched chain alkyl such as methyl, ethyl, n-propyl, isopropyl, n-butyl or isobutyl. The term "nitratoalkyl having 2 or 3 carbon atoms" refers to a group such that nitrato ($-ONO_2$) is attached at any available carbon atom of alkyl such as ethyl, n-propyl or isopropyl.

Preferred compounds of formula I are those wherein R and R', which may be the same or different, are each nitratoalkyl having 2 or 3 carbon atoms, and the nitro is at the 2- or 3-position of the phenyl ring.

The compound of formula I can be prepared as follows: Namely, a mixture of a nitrobenzaldehyde of the formula

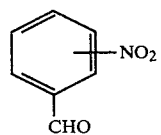
II a compound of the formula $CH_3COCH_2COOR'$    III wherein R' is as defined above, and a 3-aminocrotonic acid ester of the formula

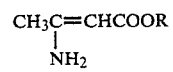
IV wherein R is as defined above is dissolved in an organic solvent or water, and then heated at reflux for few hours to give the compound of formula I.

Examples of the organic solvent are ethanol, isopropyl alcohol, dioxane, tetrahydrofuran, benzene, dimethylformamide, acetonitrile and xylene.

Alternatively, the compound of formula II is reacted with the compound of formula III in the organic solvent described above or water in the presence of a basic catalyst at 0°–110° C. for few hours, and the resulting ester of the formula

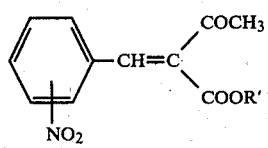
V wherein R' is as defined above, is then reacted with the compound of formula IV at a temperature of 50°–100° C., preferably 80°–90° C. to give the compound of formula I.

Examples of the basic catalyst are secondary amines (e.g. piperazine, morpholine and diethylamine), alkali alkoxides (e.g. sodium ethoxide) and sodium hydroxide.

The compound of formula I wherein R and R' are the same nitratoalkyl can be also prepared by heating a mixture of the compound of formula II, the compound of formula III and ammonia in an organic solvent described above or water at a reflux temperature.

The compound of formula I thus obtained can be purified by a conventional manner such as extraction, column chromatography and/or recrystallization.

The compound of formula III can be prepared by reacting diketene (i.e. 4-methylene-2-oxetanone) with an alcohol of the formula

R'—OH wherein R' is as defined above, in the presence of a basic catalyst at 40°–100° C., preferably 45°–55° C.

Examples of the basic catalyst are triethylamine, sodium acetate and alkoxide.

The compound of formula III wherein R' is nitratoalkyl can be also prepared by a method which comprises reacting diketene with an alcohol of the formula

R''—OH wherein R'' is haloalkyl wherein the alkyl moiety is that of the nitratoalkyl as defined for R' in the presence of a basic catalyst described above at 40°–100° C., preferably 45°–55° C., and then reacting the resulting ester with silver nitrate.

The compound of formula IV can be prepared by bubbling ammonia gas into a solution of acetoacetate of the formula $CH_3COCH_2COOR$ wherein R is as defined above, in an organic solvent such as ether, tetrahydrofuran, ethanol and benzene with stirring under ice-cooling.

The compounds of formula I of the present invention have high and sustained vasodilatatory activity, therefore, they are useful as therapeutic agents for cardiovascular disorders such as coronary artery disease, cerebral artery disease, hypertension and the like in mammals. For the purposes, the compounds of formula I may be administered orally, parenterally, rectally or topically in conventional dosage form such as tablets, granules, powders, capsules, ampoules, suppositories, ointments and adhesive plasters prepared according to conventional pharmaceutical practices.

The effective dosage of the compound of the present invention depends on the age, weight or response of patient. Generally, however, the daily dosage in adults may range from 0.01 to 10 mg/kg by intravenous administration, and 0.05 to 20 mg/kg by oral administration.

The present invention will now concretely be illustrated with reference to Test Examples which show pharmacological effect and toxicity of the compounds of formula I, Referential Examples in which processes for preparing the starting materials are described, Examples in which processes for preparing the compounds of formula I are described.

TEST EXAMPLE 1

Vasodilatatory effect of the compound of formula I was examined using following controls; 2,6-dimethyl-4-(2-nitrophenyl)-1,4-dihydropyridine-3,5-dicarboxylic acid dimethyl ester [U.S. Pat. No. 3,485,847; generally known as nifedipine; hereinafter referred to as Control 1]; 2,6-dimethyl-4-(2-nitrophenyl)-1,4-dihydropyridine-3,5-dicarboxylic acid bis(2-nitroethyl) ester (German Patent Laid-open No. 2847236; hereinafter referred to as Control 2); and 2,6-dimethyl-4-(3-nitrophenyl)-1,4-dihydropyridine-3,5-dicarboxylic acid bis(2-nitroethyl) ester (ibid.; hereinafter referred to as Control 3.)

Groups each consisting of 8 male and female mongrel dogs (10 to 15 kg body weight) were anesthetized with sodium pentobarbital (30 mg/kg, i.v.), operated for measurement of various arterial blood flow, and at 30 minutes after operation administered respectively every different grugs (0.3 μg) according to the method described below.

After administration, the blood flow through each artery was measured as the magnitude of the maximum dilatation using the method described below.

As for the coronary artery thoracotomy was conducted under artificial respiration, and the heparinized blood was introduced from the left common carotid to the left anterior descending artery via an extracorporeal circulatory path. A drug was injected into the catheter placed in the circulatory path and blood flow was measured by means of an electromagnetic flowmeter. The flow probe was inserted into the circulatory path.

As for the vertebral artery, an extracorporeal circulatory path was formed in the right vertebral artery and a drug was injected into the catheter placed in the circulatory path for measurement of blood flow by means of an electromagnetic flowmeter.

As for the femoral artery, a drug was injected via a cannula inserted in the branch of the artery and blood flow was measured using an electromagnetic flowmeter whose flow probe was connected to the femoral artery.

Vasodilatatory effect of the drugs are expressed as the increase in blood flow caused by the administration of the drugs.

| Sample | Vasodilatatory effect (maximum relative activity) | | |
|---|---|---|---|
| | Coronary artery | Vertebral artery | Femoral artery |
| Control 1 | 1.00 | 1.00 | 1.00 |
| Control 2 | 0.60 | 0.28 | 0.20 |
| Control 3 | 0.09 | 0.07 | 0.06 |
| Compound 1 | 1.27 | 1.57 | 1.33 |
| Compound 2 | 1.31 | 1.24 | 1.46 |
| Compound 3 | 1.20 | 1.50 | 1.00 |
| Compound 4 | 1.47 | 1.18 | 2.36 |
| Compound 5 | 1.15 | 1.15 | 1.89 |
| Compound 6 | 1.16 | 1.18 | 1.87 |
| Compound 7 | 1.14 | 1.19 | 1.64 |

(Note)
Compound 1: 2,6-dimethyl-4-(3-nitrophenyl)-1,4-dihydro-pyridine-3,5-dicarboxylic acid 3-ethyl ester-5-(2-nitratoethyl) ester
Compound 2: 2,6-dimethyl-4-(2-nitrophenyl)-1,4-dihydro-pyridine-3,5-dicarboxylic acid 3-ethyl ester-5-(3-nitratopropyl) ester
Compound 3: 2,6-dimethyl-4-(2-nitrophenyl)-1,4-dihydro-pyridine-3,5-dicarboxylic acid bis(2-nitratoethyl) ester
Compound 4: 2,6-dimethyl-4-(2-nitrophenyl)-1,4-dihydro-pyridine-3,5-dicarboxylic acid 3-(2-nitratoethyl) ester-5-(3-nitrapropyl) ester
Compound 5: 2,6-dimethyl-4-(3-nitrophenyl)-1,4-dihydro-pyridine-3,5-dicarboxylic acid 3-(2-nitratopropyl) ester-5-(3-nitratopropyl) ester
Compound 6: 2,6-dimethyl-4-(3-nitrophenyl)-1,4-dihydro-pyridine-3,5-dicarboxylic acid 3-(1-nitrato-2-propyl) ester-5-(3-nitratopropyl) ester
Compound 7: 2,6-dimethyl-4-(3-nitrophenyl)-1,4-dihydro-pyridine-3,5-dicarboxylic acid 3-(2-nitratoethyl)ester-5-(2-nitratopropyl) ester

TEST EXAMPLE 2

Vasodilatatory and hypotensive effects of control 1, compounds 4 and 5 were studied. Groups each consisting of 6 male and female mongrel dogs (8 to 18 kg body weight) were anesthetized with sodium pentobarbital (30 mg/kg i.v.). Compounds were administered intravenously.

Aortic blood pressure was measured with a pressure transducer connected to a rigid polyethylene tubing introduced via a femoral artery.

As for the coronary artery, the left circumflex artery was dissected from surrounding tissue at the proximal portion and an electromagnetic flow probe was placed around it under open chest and artificial respiration.

Coronary blood flow was measured by means of an electromagnetic flowmeter.

As for the vertebral artery, the blool flow was also measured by means of an electromagnetic flowmeter under spontaneous respiration.

Each drug, dissolved in 50 percent ethanol (500 μg/ml), was injected via femoral vein.

As a result of the above tests, the ratio of the decrease in blood pressure caused by the administration of control 1: compound 4: compound 5 was 1:2.5:2.

Furthermore, the ratio of the increase in coronary blood flow as well as vertebral blood flow caused by the administration of control 1: compound 4: compound 5 was nearly the same in the case of the decrease in blood pressure described above.

TEST EXAMPLE 3

Hypotensive effects of control 1, compounds 4 and 5, orally administered, were studied in conscious dogs.

The experiments were performed on 18 dogs consisting of 11 mongrel and 7 beagle dogs (7 to 15 kg body weight) of both sexes. Under sodium thiopental (25 mg/kg i.v.) anesthesia, an arterial catheter was introduced into the descending aorta via a femoral artery and was exteriorized at the neck of the dogs. Aortic blood pressure was measured with a pressure transducer connected to the arterial catheter.

The experiments were initiated 7 days after surgery. Each dog was administered control 1, compounds 4 and 5, in turn, every 2 days, and each time the effect of the compound administered was measured. No special order of the administration of the compounds was observed.

The compounds were dissolved in polyethylene glycol 400 (volume 10 mg/kg) and administered p.o. (0.6 mg/kg, 1 mg/kg) in gelatine capsules. Aortic blood pressure and heart rate were monitored in conscious-(unrestrained) dogs.

The magnitude of hypotensive action of compound 4 and 5 was almost the same as that of control 1, but the duration of the action of compounds 4 and 5 was 1.5 to 2 times longer than that of control 1.

TEST EXAMPLE 4

The subacute oral toxicity of compound 5 was investigated in male Wistar rats.

Groups of six male rats received orally compound 5 once daily, at doses of 30, 100 and 300 mg/kg/day for 14 consecutive days. No death occured during the study. A reduced body weight gain in the males of 300 mg/kg/day, was considered to be caused by decrease of food intake. However, macroscopic examination at necropsy did not reveal any treatment related changes.

REFERENTIAL EXAMPLE 1

(1) To 30 g of ethylene bromohydrin in ice bath were added by turns 22 g of diketene and 1.5 g of triethylamine with stirring while the reaction temperature was controlled at 30°–40° C. The reaction was continued at room temperature for 3 hours. To the reaction solution was added dichloromethane, the mixture was washed successively with diluted hydrochloric acid, a saturated aqueous sodium hydrogencarbonate solution and water and dried over anhydrous sodium sulfate. The solvent was distilled off and the residue was purified by distillation to obtain 45.3 g of 2-bromoethyl acetoacetate.

$bp_4$ 104°–107° C.

(2) To a solution of 85.4 g of silver nitrate in 250 ml of acetonitrile was added dropwise a solution of 70 g of 2-bromoethyl actoacetate in 50 ml of acetonitrile with stirring. The reaction was continued at room temperature for 2 days. The reaction mixture was heated at reflux for 2 hours, poured into ice water and extracted with ether. The ether layer was washed with a saturated aqueous sodium chloride solution and dried over anhydrous sodium sulfate. The ether was distilled off to give 58.5 g of 2-nitratoethyl acetoacetate.

NMR (CDCl$_3$): δ: 2.25(3H, s, —COCH$_3$), 3.47(2H, s, —COCH$_2$CO$_2$—), 4.38(2H, m, —CH$_2$ONO$_2$), 4.60(2H, m, —CO$_2$CH$_2$—)

IR$\nu_{max}^{neat}$ cm$^{-1}$: 1750(CO$_2$H), 1715(CO), 1630, 1280, 850(ONO$_2$)

MS m/e: 191 (M+)

REFERENTIAL EXAMPLE 2

An ammonia gas was bubbled through a solution of 40 g of 2-nitratoethyl acetoacetate in 40 ml of tetrahydrofuran under ice-cooling with stirring for 8 hours and the reaction mixture was left to stand for an hour. The solvent was distilled off to obtain 30 g of 2-nitratoethyl 3-aminocrotonate.

NMR (CDCl$_3$): δ: 1.90(3H, s, CH$_3$C(NH$_2$)=), 4.20–4.47(2H, m, —CO$_2$CH$_2$—), 4.48–4.77 (2H, m, —CH$_2$ONO$_2$)

IR$\nu_{max}^{neat}$ cm$^{-1}$: 3460, 3420, 1555(—NH$_2$), 1660(—CO$_2$—), 1625, 1270, 850(ONO$_2$)

MS m/e: 190 (M+)

REFERENTIAL EXAMPLE 3

To 25 g of 2-nitratoethanol were added by turns 20 g of diketene and 1 g of triethylamine under ice-cooling with stirring while the reaction temperature was controlled at 30°–40° C. The reaction was continued at room temperature for 3 hours. To the reaction solution was added dichloromethane, the mixture was washed successively with diluted hydrochloric acid, a saturated aqueous sodium hydrogencarbonate solution and water and dried over anhydrous sodium sulfate. The solvent was distilled off to give 35.8 g of 2-nitratoethyl acetoacetate.

The physical constants of the product are the same as those in Referential Example 1(2).

REFERENTIAL EXAMPLE 4

(1) 90 g of 3-bromopropanol was added to 8 g of sodium acetate, to which 59.8 g of diketene was added dropwise controlling the reaction mixture at 40°–50° C. The mixture was further stirred at room temperature for 3 hours. The reaciton mixture was poured into ice water containing a diluted aqueous sodium hydroxide solution. The mixture was extracted with dichloromethane and the dichloromethane layer was washed with a saturated aqueous sodium chloride solution and dried over anhydrous sodium sulfate. The solvent was distilled off to obtain 102.6 g of 3-bromopropyl acetoacetate.

$bp_1$ 109°–113° C.

(2) To a solution of 107 g of silver nitrate in 500 ml of acetonitrile was added dropwise 100 g of 3-bromopropyl acetoacetate with stirring. The mixture was left to stand overnight, heated at reflux for 2 hours poured into ice water and extracted with ether. The ether layer was washed with a saturated aqueous sodium chloride solution and dried over anhydrous sodium sulfate. The ether was distilled off to give 88 g of 3-nitratopropyl acetoacetate.

NMR (CDCl$_3$): δ: 2.07(2H, m, —CH$_2$CH$_2$CH$_2$—), 2.23(3H, s, —COCH$_3$), 3.43(2H, s, —COCH$_2$CO$_2$—), 4.20(2H, t, J=6 Hz, —CO$_2$CH$_2$—), 4.50(2H, t, J=6 Hz, —CH$_2$ONO$_2$)

IR$\nu_{max}^{neat}$cm$^{-1}$: 1745(CO$_2$H), 1715(CO), 1625, 1280, 860(ONO$_2$)

MS m/e: 205 (M+)

REFERENTIAL EXAMPLE 5

An ammonia was bubbled through a solution of 30 g of 3-nitratopropyl acetoacetate in 35 ml of tetrahydrofuran under ice-cooling with stirring for 8 hours. The mixture was left to stand for an hour. The solvent was distilled off to obtain 25 g; of 3-nitratopropyl 3-aminocrotonate.

NMR (CDCl$_3$): δ: 1.83–2.30(2H, m, —CH$_2$CH$_2$CH$_2$ONO$_2$), 1.93(3H, s, —CH$_3$C(NH$_2$)=), 4.17(2H, t, J=6 Hz, —CO$_2$CH$_2$—), 4.57(2H, t, J=6 Hz, —CH$_2$ONO$_2$)

IR$\nu_{max}^{neat}$ cm$^{-1}$: 3460, 3420, 1555(—NH$_2$), 1655(—CO$_2$—), 1615, 1270, 860(ONO$_2$)

MS m/e: 204 (M+)

REFERENTIAL EXAMPLE 6

(1) 0.7 g of sodium acetate was added to 7.5 g of 2-chloropropanol, to which 7.4 g of diketene was added dropwise with stirring while the reaction temperature was maintained at 40°–50° C. The reaction mixture was stirred at room temperature for an additional 2 hours and then worked up in the manner described in Referential Example 4. The resulting crude product was purified by distillation to obtain 9.8 g of 2-chloropropyl acetoacetate.

bp$_5$ 88°–92° C.

(2) 26.7 g of pyridine was added to a solution of 54 g of silver nitrate in 300 ml of acetonitrile, to which 40 g of 2-chloropropyl acetoacetate was added dropwise with stirring. The mixture was heated at reflux for 10 hours, poured into ice water and extracted with ether. The ether layer was washed with a saturated aqueous sodium chloride solution and dried over anhydrous sodium sulfate. The ether was distilled off and the resulting residue was subjected to column chromatography on silica gel (n-hexane-acetone=3:1) to give 17 g of 2-nitratopropyl acetoacetate.

NMR (CDCl$_3$): δ: 1.23–1.43(3H, m, O$_2$NOCHCH$_3$), 2.27(3H, s, —COCH$_3$), 3.47(2H, d, J=2 Hz, —COC$\overline{\text{H}}$$_2$CO$_2$—), 4.17–4.63(2H, m, —CO$_2$CH$_2$—), 5.00–5.60(1H, m, CHONO$_2$)

IRν$_{max}$$^{neat}$ cm$^{-1}$: 1740(CO$_2$H), 1710(CO), 1615, 1280, 860(ONO$_2$)

MS m/e: 205 (M+)

bp$_8$ 113°–119° C.

REFERENTIAL EXAMPLE 7

4.1 g of sodium acetate was added to 55 1 g of 2-nitratopropanol, to which 46.2 g of diketene was added dropwise while keeping the reaction temperature at 40° to 50° C. with stirring. The stirring was continued for an additional 1 to 2 hours at room temperature. The reaction mixture was poured into a saturated aqueous sodium hydrogencarbonate solution, and extracted with ether. The ether layer was washed with a saturated aqueous sodium chloride solution, dried over anhydrous sodium sulfate, and the solvent was evaporated to give a residue which was then subjected to column chromatography on silica gel (eluted with n-hexane-dichloromethane=1:1) to give 89.7 g of 2-nitratopropyl acetoacetate.

The physical constants of the product are the same as those in Referential Example 6(2).

REFERENTIAL EXAMPLE 8

Following the reaction and working up similar to those of Referential Example 4 and using 21 g of 1-nitrato-2-propanol, 1 g of sodium acetate and 17 g of diketene, there was obtained 27.7 g of 1-nitrato-2-propyl acetoacetate.

NMR (CDCl$_3$): δ: 1.28(3H, d, J=5 Hz, CHCH$_3$), 2.23(3H, s, —COCH$_3$), 3.44(2H, d, J=2 Hz, —COC$\overline{\text{H}}$$_2$CO$_2$—), 4.13–4.60(2H, M, —CH$_2$ONO$_2$), 4.93–5.50(1H, m, CO$_2$CH)

IRν$_{max}$$^{neat}$ cm$^{-1}$: 1745(CO$_2$H), 1715(CO), 1630, 1280, 850(ONO$_2$)

MS m/e: 205 (M+)

EXAMPLE 1

In 30 ml of isopropyl alcohol were dissolved 1 g of 2-nitratoethyl acetoacetate, 0.68 g of ethyl 3-aminocrotonate and 0.79 g of 3-nitrobenzaldehyde. The solution was heated at reflux for 3 hours. The solvent was distilled off and the residue was poured into water. The mixture was extracted with dichloromethane and the dichloromethane layer was washed with water and dried over anhydrous sodium sulfate. The solvent was distilled off and ether was added to the residue to produce crystals, which was then recrystallized from acetone-n-hexane to give 1.17 g of 2,6-diemthyl-4-(3-nitrophenyl)-1,4-dihydropyridine-3,5-dicarboxylic acid 3-ethyl ester-5-(2-nitratoethyl) ester.

m.p. 146°–147° C.

EXAMPLE 2

In 30 ml of isopropyl alcohol were dissolved 1.2 g of 2-nitratoethyl acetoacetate, 0.73 g of methyl 3-aminocortonate and 0.95 g of 2-nitrobenzaldehyde. The solution was subjected to reflux, extraction, washing, dryness and evaporation of the solvent in the manner described in Example 1, and the resulting residue was subjected to column chromatography on silica gel (eluted with n-hexane-acetone=5:2) and recrystallized from ether-petroleum ether to give 0.87 g of 2,6-dimethyl-4-(2-nitro-phenyl)-1,4-dihydropyridine-3,5-dicarboxylic acid 3-methyl ester-5-(2-nitratoethyl) ester.

m.p. 110°–111.5° C.

EXAMPLE 3

In 30 ml of isopropyl alcohol were dissolved 1 g of 2-nitratoethyl acetoacetate, 0.75 g of isopropyl 3-aminocrotonate and 0.79 g of 2-nitrobenzaldehyde. The solution was treated in the manner described in Example 1 and the resulting residue was subjected to column chromatography on silica gel (eluted with n-hexane-acetone=5:2) and recrystallized from ether-petroleum ether to obtain 0.75 g of 2,6-dimethyl-4-(2-nitrophenyl)-1,4-dihydropyridine-3,5-dicarboxylic acid 3-isopropyl ester-5-(2-nitratoethyl) ester.

m.p. 142°–144° C.

EXAMPLE 4

In 30 ml of isopropyl alcohol were dissolved 1.5 g of 2-nitratoethyl acetoacetate, 1.3 g of isobutyl 3-aminocrotonate and 1.2 g of 3-nitrobenzaldehyde. The solution was treated in the manner described in Example 1, the resulting residue was then subjected to column chromatography on silica gel (eluted with n-hexane-acetone=3:1), and recrystallized from ether-petroleum ether to give 1.1 g of 2,6-dimethyl-4-(3-nitrophenyl)-1,4-dihydropyridine-3,5-dicarboxylic acid 3-isobutyl ester-5-(2-nitratoethyl) ester.

m.p. 114°–116° C.

EXAMPLE 5

In 30 ml of isopropyl alcohol were dissolved 1 g of 3-nitratopropyl acetoacetate, 0.63 g of ethyl 3-aminocrotonate and 0.74 g of 2-nitrobenzaldehyde. The solution was treated in the manner described in Example 1 to obtain a residue, which was then subjected to column chromatography on silica gel (eluted with n-hexane-acetone=5:2) to obtain 0.75 g of viscous 2,6-dimethyl-4-(2-nitrophenyl)-1,4-dihydropyridine-3,5-dicarboxylic acid 3-ethyl ester-5-(3-nitratopropyl) ester.

NMR (CDCl$_3$) δ: 1.15(3H, t, J=7 Hz, —CH$_2$CH$_3$), 1.98(2H, m, —CO$_2$CH$_2$CH$_2$CH$_2$—), 2.32(6H, s, —C$\overline{\text{H}}$$_3$ at the 2,6-positions), 3.8–4.5(6H, —CO$_2$ZCH$_2$— x2)

IRν$_{max}$$^{neat}$ cm$^{-1}$: 3320(NH), 1685, 1300, 1210(—CO$_2$—), 1625, 1275, 855(ONO$_2$)

MS m/e: 449 (M+)

EXAMPLE 6

In 70 ml of isopropyl alcohol saturated with ammonia were dissolved 5 g of 2-nitratoethyl acetoacetate and 2 g of 2-nitrobenzaldehyde. The solution was heated at reflux for 5 hours and then treated in the manner described in Example 1 to give 2.51 g of 2,6-dimethyl-4-(2-nitrophenyl)-1,4-dihydropyridine-3,5-dicarboxylic acid bis(2-nitratoethyl) ester.

m.p. 131°–132° C.

EXAMPLE 7

In 30 ml of isopropyl alcohol were dissolved 2 g of 3-nitratopropyl acetoacetate and 0.74 g of 2-nitrobenzaldehyde. To the solution was added 4 ml of isopropyl alcohol saturated with an ammonia gas at 10° C. The mixture was treated in the manner described in Example 1 to obtain a residue, which was then subjected to column chromatography on silica gel (eluted with n-hexane-acetone=5:3) and recrystallized from ether to obtain 1.11 g of 2,6-dimethyl-4-(2-nitrophenyl)-1,4-dihydropyridine-3,5-dicarboxylic acid bis(3-nitratopropyl) ester.

m.p. 101°–102.5° C.

EXAMPLE 8

In 30 ml of isopropyl alcohol was dissolved 1 g of 2-nitratoethyl acetoacetate, 1.1 g of 3-nitratopropyl 3-aminocrotonate and 0.79 g of 2-nitrobenzaldehyde. The solution was treated in the manner described in Example 1 to obtain a residue, which was then subjected to column chromatography on silica gel (eluted with n-hexane-acetone=5:2) and recrystallized from ether to obtain 1.11 g of 2,6-dimethyl-4-(2-nitrophenyl)-1,4-dihydropyridine-3,5-dicarboxylic acid 3-(2-nitratoethyl) ester-5-(3-nitratopropyl) ester.

m.p. 120.5°–121.5° C.

EXAMPLE 9

In 100 ml of benzene were dissolved 10 g of 2-nitratoethy acetoacetate, 7.91 g of 2-nitrobenzaldehyde and 0.7 ml of piperidine. The solution was reacted under azeotropic dehydration for 1.5 hours, and poured into ice water. Dilute hydrochloric acid was added, and the mixture was extracted with ethyl acetate. The ethyl acetate layer was washed, in turn, with 15% aqueous sodium hydrogen sulfite solution, 15% aqueous sodium carbonate solution and saturated aqueous sodium chloride solution, and then dried over anhydrous sodium sulfate. Evaporation of the solvent gave a residue, to which 10.68 g of 3-nitratopropyl 3-aminocrotonate was then added. The mixture was heated at 75°–85° C. for 4 hours with stirring, and ice water was poured into this mixture. The mixture was extracted with dichloromethane, and the dichloromethane layer was washed with water and dried over anhydrous sodium sulfate. Evaporation of the solvent gave a residue which was then subjected to column chromatography on silica gel (eluted with dichloromethane) and recrystallized from ether to obtain 12.1 g of 2,6-dimethyl-4-(2-nitrophenyl)-1,4-dihydropyridine-3,5-dicarboxylic acid 3-(2-nitratoethyl) ester-5-(3-nitratopropyl) ester.

m.p. 120.5°–121.5° C.

EXAMPLE 10

In 30 ml of isopropyl alcohol were dissolved 1.1 g of 2-nitratopropyl acetoacetate, 1.1 g of 3-nitratopropyl 3-aminocrotonate and 0.79 g of 3-nitrobenzaldehyde. The solution was treated in the manner described in Example 1 to obtain a residue, which was then subjected to column chromatography on silica gel (eluted with n-hexane-ethyl acetate=5:1) and recrystallized from ether to obtain 1.22 g of 2,6-dimethyl-4-(3-nitrophenyl)-1,4-dihydropyridine-3,5-dicarboxylic acid 3-(2-nitratopropyl) ester-5-(3-nitratopropyl) ester.

m.p. 82°–83° C.

EXAMPLE 11

In 100 ml of benzene were dissolved 6 g of 2-nitratopropyl acetoacetate, 4.42 g of 3-nitrobenzaldehyde and 0.4 ml of piperidine. The solution was subjected to reflux, extraction, washing, dryness and evaporation of the solvent in the manner described in Example 9 to give a residue, to which 5.97 of 3-nitratopropyl 3-aminocrotonate was added. The mixture was treated in the manner described in Example 9 to give a residue, which was then subjected to column chromatography on silica gel (eluted with n-hexane-ethyl acetate=5:1) and recrystallized from ether to obtain 7.7 g of 2,6-dimethyl-4-(3-nitrophenyl)-1,4-dihydropyridine-3,5-dicarboxylic acid 3-(2-nitratopropyl) ester-5-(3-nitratopropyl) ester.

m.p. 82°–83° C.

EXAMPLE 12

In 50 ml of isopropyl alcohol were dissolved 3.5 g of 1-nitrato-2-propyl acetoacetate, 3.5 g of 3-nitratopropyl 3-aminocrotonate and 2.58 g of 3-nitrobenzaldehyde. The solution was treated in the manner described in Example 1 to obtain a residue, which was then subjected to column chromatography on silica gel (eluted with n-hexane-ethyl acetate=5:2) and recrystallized from ether to obtain 3.2 g of 2,6-dimethyl-4-(3-nitrophenyl)-1,4-dihydropyridine-3,5-dicarboxylic acid 3-(1-nitrato-2-propyl) ester-5-(3-nitratopropyl) ester.

m.p. 101°–103° C.

EXAMPLE 13

In 350 ml of benzene were dissolved 29 g of 1-nitrato-2-propyl acetoacetate, 20 g of 3-nitrobenzaldehyde and 1.9 ml of piperidine. The solution was subjected to reflux, extraction, washing, dryness and epvaporation of the solvent in the manner described in Example 9 to give a residue, to which 28.9 g of 3-nitratopropyl 3-aminocrotonate was then added. The mixture was treated in the manner described in Example 9 to give a residue, which was then subjected to column chromatography on silica gel (eluted with n-hexane-ethyl acetate=5:2) and recrystallized from ether to obtain 40.2 g of 2,6-dimethyl-4-(3-nitrophenyl)-1,4-dihydropyridine-3,5-dicarboxylic acid 3-(1-nitrato-2-propyl) ester-5-(3-nitratopropyl) ester.

m.p. 101°–103° C.

EXAMPLE 14

In 50 ml of benzene were dissolved 4 g of 2-nitratopropyl acetoacetate, 2.9 g of 3-nitrobenzaldehyde and 0.3 ml of piperidine. The solution was subjected to reflux, extraction, washing, dryness and evaporation of the solvent in the manner described in Example 9 to give a residue, to which 3.5 g of 2-nitratoethyl 3-aminocrotonate was then added. The mixture was treated in the manner described in Example 9 to give a residue, which was then subjected to column chromatography on silica gel (eluted with n-hexane-ethyl acetate=2:1) and recrystallized from ether to obtain 2.1 g of 2,6-dimethyl-4-(3-nitrophenyl)-1,4-dihydropyridine-3,5-dicarboxylic acid 3-(2-nitratoethyl) ester-5-(2-nitratopropyl) ester.

m.p. 89°–91° C.

What is claimed is:

1. The compounds of the formula

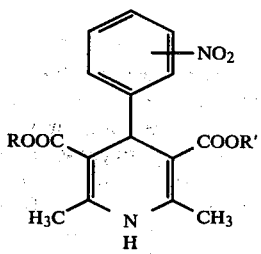

wherein R is alkyl having 1 to 4 carbon atoms or nitratoalkyl having 2 or 3 carbon atoms, and R' is nitratoalkyl having 2 or 3 carbon atoms.

2. A compound according to claim 1 wherein R and R', which may be the same or different, are each nitratoalkyl having 2 or 3 carbon atoms, and the nitro occurs at the 2- or 3-position of the phenyl ring.

3. 2,6-dimethyl-4-(2-nitrophenyl)-1,4-dihydro-pyridine-3,5-dicarboxylic acid 3-(2-nitratoethyl) ester-5-(3-nitratopropyl) ester.

4. 2,6-dimethyl-4-(3-nitrophenyl)-1,4-dihydro-pyridine-3,5-dicarboxylic acid 3-(2-nitratopropyl) ester-5-(3-nitratopropyl) ester.

5. A method for treating cardiovascular disorders in a mammal where administration of a vasodilator is indicated comprising administering to said mammal a pharmaceutically effective amount of a compound of the formula

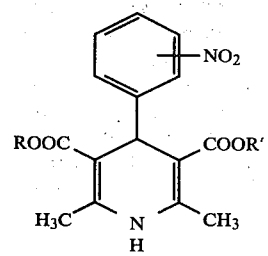

wherein R is alkyl having 1 to 4 carbon atoms or nitratoalkyl having 2 or 3 carbon atoms, and R' is nitratoalkyl having 2 or 3 carbon atoms.

* * * * *